US010125065B2

(12) United States Patent
Siller et al.

(10) Patent No.: US 10,125,065 B2
(45) Date of Patent: Nov. 13, 2018

(54) METHOD FOR THE SEPARATION OF DIAMOND PARTICLE CLUSTERS

(71) Applicant: University of Newcastle Upon Tyne, Newcastle-upon-Tyne (GB)

(72) Inventors: Lidija Siller, Whitley Bay (GB); Yuriy Butenko, Leiden (NL)

(73) Assignee: University of Newcastle Upon Tyne (GB)

( * ) Notice: Subject to any disclaimer, the term of this patent is extended or adjusted under 35 U.S.C. 154(b) by 419 days.

(21) Appl. No.: 14/396,093

(22) PCT Filed: Apr. 26, 2013

(86) PCT No.: PCT/GB2013/051082
§ 371 (c)(1),
(2) Date: Oct. 22, 2014

(87) PCT Pub. No.: WO2013/160704
PCT Pub. Date: Oct. 31, 2013

(65) Prior Publication Data
US 2015/0291489 A1    Oct. 15, 2015

(30) Foreign Application Priority Data

Apr. 27, 2012 (GB) .................................. 1207327.6

(51) Int. Cl.
*C07C 9/22*    (2006.01)
*C07C 2/86*    (2006.01)
*C01B 32/28*   (2017.01)

(52) U.S. Cl.
CPC ................ *C07C 9/22* (2013.01); *C01B 32/28* (2017.08); *C07C 2/86* (2013.01)

(58) Field of Classification Search
None
See application file for complete search history.

(56) References Cited

U.S. PATENT DOCUMENTS

| 2010/0298600 | A1 | 11/2010 | Lee |
| 2012/0003479 | A1 | 1/2012 | Hsin et al. |
| 2012/0304545 | A1* | 12/2012 | Park .................... C09D 7/1216 51/307 |

FOREIGN PATENT DOCUMENTS

| CN | 1429144 | 7/2003 |
| EP | 2535312 | 12/2012 |
| KR | 20110093700 | 8/2011 |

OTHER PUBLICATIONS

International Search Report for related PCT Application PCT/GB2013/051082, dated Oct. 14, 2013 (4 pages).

(Continued)

*Primary Examiner* — Guinever S Gregorio
(74) *Attorney, Agent, or Firm* — Winthrop & Weinstine, P.A.

(57) ABSTRACT

A method for the separation of diamond particle clusters into discrete diamond particles and/or into smaller diamond particle clusters comprising fewer diamond particles is disclosed.

The diamond particle clusters are combined with at least one liquid phase organic or inorganic compound, or with a solution of at least one organic or inorganic compound in at least one solvent to form a reaction mixture. Mechanical means are then used to separate the diamond particle clusters into discrete diamond particles and/or into smaller clusters within the reaction mixture producing diamond particles with dangling bonds or free bonding sites on the surface of the diamond particles. The at least one organic or inorganic compound then reacts with these dangling bonds present on the diamond particle surface. The surfaces of the diamond particles are functionalized by the reaction with the organic or inorganic compounds and the diamond particles and/or smaller clusters produced are well dispersed in dry powder form, as well as in solution.

17 Claims, 4 Drawing Sheets

(56) References Cited

OTHER PUBLICATIONS

Li et al. "Surface functionalization of nanodiamond particles via atom transfer radical polymerization", Carbon, vol. 44, Issue 11, Sep. 2006 (pp. 2308-2315).
Ozawa, M. et al. "Preparation and Behavior of Brownish, Clear Nanodiamond Colloids", Advanced Materials, vol. 19, Issue 9, May 2007 (pp. 1201-1206).
Shintaro et al. "Chemical Modification of the Diamond Surface Using Benzoyl Peroxide and Dicarboxylic Acids", Langmuir, vol. 19, No. 23, Nov. 1, 2003 (pp. 9693-9698).
Siller, L. et al. "Recent advances in functionalisation of silicon nanocrystals and ultradispersed nanodiamonds", 219th ECS Meeting, The Electrochemical Society, Abstract #1237, Dec. 31, 2011.

* cited by examiner

METHOD FOR THE SEPARATION OF DIAMOND PARTICLE CLUSTERS

FIELD OF THE INVENTION

The invention relates to a process for separating clusters of diamond particles, and in particular to clusters of micron and nano-sized diamond particles. The invention also relates to a process for the functionalization of separated diamond particles, and in particular to the functionalization of separated micron and nano-sized diamond particles.

BACKGROUND TO THE INVENTION

Diamond particles, including diamond nanoparticles or nanodiamonds, have potential uses in a wide variety of applications including plating, lubricating oils, polishing, coating agents for metal surfaces, abrasives, and biomedical devices.

Nanodiamonds may be produced by the detonation of explosives with a negative oxygen balance in hermetic tanks. These detonation nanodiamonds have particle sizes typically in the range 1-50 nm and are particularly prone to agglomeration, forming tightly aggregated secondary particles or clusters.

Nanodiamonds and micron-sized diamond particles may also be synthesised by high temperature and high pressure (HTHP) methods. These diamond particles typically have particle sizes in the range 1 nm-1000 micron. Alternative sources of nano- or micron-sized diamond particles include diamond particles formed by HTHP methods and natural micron diamond powder. These diamond particles are also prone to aggregation forming aggregated secondary particles or clusters. Sizes of aggregated diamond particles vary widely but can be up to several 100s of microns in size.

A known method for separating these tightly aggregated nanodiamond clusters is via wet-stirred-media-milling in water using micrometer-sized beads to break up the aggregates and simultaneously dispersing them in water. This method has been used to form clear colloidal solutions of nanodiamonds (Adv. Mater. 2007, 19, 1201-1206). This method is only suitable for the formation of nanodiamond dispersions in solvents since the nanodiamonds tend to re-agglomerate after drying.

US2010/0298600 describes a method for the chemical functionalization of the surface of nanodiamonds in a liquid phase. The method uses a wet milling process similar to that described above, prior to treatment with acid. The method attempts to de-aggregate particles using an acid treatment step, which leads to formation of carboxylic acid groups on the surface of the nanodiamonds. There is no step in the process which actually breaks apart the clusters of nanodiamonds. In addition, the presence of carboxylic acid groups on the surface of the nanodiamonds will actually promote aggregation of the nanodiamonds after drying.

EP2535312 describes a method for dispersing nanodiamonds in solution. The method involves a wet milling process in the presence of an aqueous metal hydroxide and chemically binding a metal ion from the metal hydroxide solution with a reactive group present on the nanodiamond surface. For example a carboxylic acid group present on the nanodiamond surface may react with the metal hydroxide to form nanodiamond-metal salts as shown in Reaction 1 below, where 'ND' is used to represent the nanodiamond.

$$ND\text{-}COOH + MOH \rightarrow ND\text{-}COO\text{-}M^+ + H_2O \qquad \text{Reaction 1}$$

By substituting a hydrogen atom with a metal ion the electrical repulsion between the nanodiamond particles is increased, improving dispersibility of the nanodiamonds in solution and larger ionic diameters lead to better dispersions. Although this method does involve a step in which a dry nanodiamond powder is obtained, the nanodiamonds do tend to re-aggregate after drying, but then re-disperse when mixed with a dispersion solvent. This method is also restricted to nanodiamond dispersions in which the diamond particles are functionalised with metals which could limit the end use of the nanodimond product.

It would be desirable to provide an improved method for the separation of secondary diamond particle clusters into discrete particles, providing diamond particles that are well dispersed in dry powder form, as well as in solution. In addition, it would be desirable to provide a method in which the surface functionalisation of the nanodiamond particles can be altered to suit the end use of the product.

SUMMARY OF THE INVENTION

According to a first aspect of the present invention, a method for the separation of diamond particle clusters having a diameter of less than or equal to 1.0 mm into discrete diamond particles and/or into smaller clusters comprising fewer diamond particles, comprises the steps of
a) combining the diamond particle clusters with at least one liquid phase organic or inorganic compound, or with a solution of at least one organic or inorganic compound in at least one solvent to form a reaction mixture, wherein the at least one organic or inorganic compound reacts with dangling-bonds present on the diamond particle surface; and
b) using mechanical means to break up the diamond particle clusters into discrete diamond particles and/or into smaller clusters comprising fewer diamond particles within the reaction mixture;
wherein step b) produces diamond particles with dangling bonds on the surface of the diamond particles and wherein the at least one organic or inorganic compound reacts with at least some of the dangling bonds on the diamond particles. Step b) of the method involves imparting kinetic energy to the diamond particle clusters, causing the clusters or aggregates to break apart into individual diamond particles and/or into smaller diamond particle clusters containing fewer diamond particles. Preferably, step b) includes shaking or stirring or ultrasonication of the reaction mixture. Dangling bonds or free bonding sites are formed in places where the diamond clusters break apart. The at least one organic or inorganic compound(s) added in, step a) reacts with these dangling bonds, saturating the bonds. This prevents re-aggregation of the individual diamond particles or re-aggregation of the smaller diamond particle clusters since the active sites (dangling bonds) on the surface of the diamond particles are occupied through reaction with the organic or inorganic compound(s) added in step a). The nature of the chemical groups added to the surface of the diamond particles is governed by the organic or inorganic compound(s) used in step a) of the method.

The dangling bonds may be carbon bonds. The dangling bonds may relate to other atoms present on the surface of the diamond particle.

Preferably, the method produces discrete diamond particles. The product may include smaller diamond particle clusters comprising fewer diamond particles.

Preferably, the reaction mixture formed in step a) is in the form of a slurry.

The at least one organic or inorganic compound(s) may be dissolved in at least one solvent to form a solution prior to combining with the diamond particle clusters. Preferably the solvent is inert. Preferably the at least one solvent is an organic solvent. The at least one organic or inorganic compound(s) may be dissolved in a mixture of solvents. Solvent mixtures may be used to help improve solubility of the organic or inorganic compound(s).

A mixture of more than one organic or inorganic compounds may be used in step a) of the method.

The at least one organic or inorganic compound may be any compound that reacts with free radicals.

Preferably the inorganic compound is not a metal containing compound and preferably the separated diamond particle product is not a metal salt. More preferably, the inorganic compound is not a metal hydroxide.

The at least one organic or inorganic compound may be a compound which generates free radicals within the reaction mixture. Suitable compounds include halogen molecules, azo compounds and organic peroxides.

Preferably, the at least one organic or inorganic compound is selected to provide a surface functionalisation of the diamond or nanodiamond particles to suit the end use of the product.

Preferably, step b) is a mechanical milling step and further includes the introduction of milling beads to the reaction mixture. When milling beads are present shaking or stirring the reaction mixture or by applying ultrasonication to the mixture causes the milling beads to collide with the diamond particle clusters. This causes the clusters to break apart into individual diamond particles and/or smaller diamond particle clusters containing fewer diamond particles.

Preferably, the milling beads are ceramic milling beads. More preferably, the milling beads are selected from the group comprising zirconia beads and silica beads and mixtures thereof.

Alternatively, the milling beads may be diamond particles which are larger in size compared to the diamond particles to be separated.

Preferably the milling beads are larger in size than the diamond particles by a factor of between 100 and 100000.

When the diamond particles are nanodiamond particles the milling beads preferably have an average diameter of less than 1 mm. More preferably the milling beads have an average diameter of less than 0.5 mm. Still more preferably the milling beads have an average diameter of less than or equal to 0.1 mm.

Preferably the diamond particles have a diameter of less than 0.5 mm.

More preferably the diamond particles are nanodiamond particles with a diameter in the range 1 to 1000 nm.

The diamond particle clusters used in the method may be from any commercial source. For example the diamond particle clusters may be nanodiamond aggregates from a detonation nanodiamond source, known as detonation nanodiamonds or DND. Alternatively, the diamond particle clusters may originate from a high temperature and high pressure (HTHP) method of diamond particle synthesis or may originate from natural micron diamond powder. Diamond particle clusters from HTHP methods may be further ground to reduce the size of the particles before being treated to separate the clusters using the method of the invention.

Where raw, untreated, detonation nanodiamond powder is used in the method of the invention, the method may include the initial step of treatment of the nanodiamonds with an oxidising mineral acid. The mineral acid may be selected from the group comprising $HClO_4$, $H_2SO_4$ and $HNO_3$.

Treatment with oxidising mineral acid purifies the detonation nanodiamond powder by removing any non-diamond forms of carbon.

Alternately the initial step may involve a treatment of raw nanodiamonds with oxygen or air or nitrogen oxides at elevated temperatures up to 700 C.

The at least one organic or inorganic compound may be any compound that reacts with free radicals and/or that reacts with unsaturated (dangling) bonds of carbon atoms present on the diamond particle surface. This includes any unsaturated organic compounds, and particularly includes alkenes, unsaturated fatty acids, and free radical inhibitors and organic peroxides. An unsaturated organic compound contains at least one unsaturated $C=C$ double bond or $C\equiv C$ triple bond. The organic compound may be a liquid phase compound, alternatively, or additionally, it may be dissolved in at least one inert solvent prior to reaction with the diamond particle clusters. Preferably the inert solvent is an organic solvent. The organic compound may be dissolved in a mixture of solvents.

Preferably, the alkenes from which the at least one organic compound may be selected comprise $C_6$ to $C_{30}$ alkenes, more preferably $C_6$ to $C_{12}$ alkenes, and mixtures thereof. Preferably the alkenes are straight chain alkenes. Use of straight chain organic compounds avoids steric hindrance for reactions to occur. Preferably the alkene double bond is located at the first position. Location of the double bond at the first position also avoids steric hindrance.

In a particularly preferred embodiment, the alkene is selected from the group comprising 1-undecene or dodecene.

In a particularly a preferred embodiment, the at least one organic compound is benzoyl peroxide.

Preferably, the unsaturated fatty acids from which the liquid phase organic compound may be selected comprise $C_2$ to $C_{28}$ unsaturated fatty acids, more preferably $C_6$ to $C_{12}$ unsaturated fatty acids.

In a particularly preferred embodiment, the unsaturated fatty acid is linoleic acid.

When the reaction mixture is shaken it is preferably shaken at a frequency of at least 10 Hz. More preferably the reaction mixture is shaken at a frequency in the range 10-40000 Hz.

When ultrasonication is applied to the reaction mixture the frequency of ultrasonication is preferably less than 80 kHz.

Shaking and/or ultrasonication is preferably performed in closed vessels. Valves may be used on reaction vessels to release any build up of pressure.

Shaking and/or ultrasonication is preferably performed under an atmosphere of inert gas. The inert gas may be selected from the group comprising nitrogen and argon.

Shaking and/or ultrasonication is preferably performed at atmospheric pressure. Shaking and/or ultrasonication may be performed at elevated pressure in order to increase the reaction rate of the at least one organic or inorganic compound(s) with the diamond particles. Shaking and/or ultrasonication may be performed at elevated pressure in order to increase the boiling temperature of the at least one solvent or the reaction mixture.

Shaking and/or ultrasonication is performed at temperatures below the boiling point of the at least one organic or inorganic compound(s), or the boiling point of the reaction mixture.

Preferably, the reaction mixture is shaken continuously, or ultrasonication applied continuously, provided that continuous cooling of the reaction mixture is applied. Preferably the reaction mixture is continuously cooled to a temperature of not more than the boiling temperature of the at least one solvent(s) and/or the at least one organic or inorganic compound(s) of the reaction mixture at the pressure at which the process is conducted. The cooling temperature depends on the organic/inorganic compound(s) and/or solvent(s) being used in the reaction mixture and should be maintained below the boiling temperature of the reaction mixture at the pressure at which the process is conducted.

Alternatively, the reaction mixture is shaken, or ultrasonication is applied, in cycles, and preferably the duration of each cycle is not more than 10 minutes.

Mechanical shaking or ultrasonication of the reaction mixture can cause a rise in temperature through the impact of diamond particle clusters with other clusters or diamond particles and through chemical reactions occurring in the mixture. When milling beads are used heat can also be generated when the beads collide with diamond particle clusters or diamond particles. Excessive heating can cause polymerisation of the at least one organic compound(s), which is not desirable for the method of the invention.

Preferably the reaction mixture is cooled between shaking or ultrasonication cycles to avoid excessive heating. Preferably the reaction mixture is cooled to a temperature of not more than 60° C. between cycles. The cooling temperature depends on the organic compound and/or solvent being used in the reaction mixture. Preferably, the maximum temperature of the mixture is be maintained below the boiling temperature of the at least one organic or inorganic compound and/or the at least one solvent and/or the reaction mixture.

When milling beads are used, the method of the invention preferably includes a further step, c) of separating the separated diamond particles and/or smaller clusters from the milling beads and the organic and/or inorganic compound(s) added in the step a). Preferably the diamond particles and/or smaller clusters are separated from the milling beads using a method selected from the group comprising filtration, centrifugation, extraction, precipitation, decantation, washing by organic solvent or solvents or water and combinations thereof.

The milling beads are much greater in size compared to the separated diamond particles so filtration may be used to separate the milling beads from the rest of the mixture.

Alternatively, the milling beads may be separated from the rest of the mixture using a centrifuge or simply by mixing. This process can be repeated several times if necessary with adding a fresh solvent each time to remove the organic and/or inorganic compound added in step a).

The slurry from step b) may be diluted with an organic solvent, or a mixture of organic solvents, prior to separation in a centrifuge or by mixing. The milling beads are much larger in size compared to the separated diamond particles, so these fall to the bottom of the mixture quickly in a centrifuge or shortly after mixing. The supernatant containing the suspended diamond particles can then be separated from the milling beads by decanting. This process can be repeated several times if necessary with adding a fresh solvent each time to remove the organic and/or inorganic compound added in step a).

Alternatively, or additionally, the separation step may be carried out using a soxhlet extractor and an organic solvent, or mixture of solvents, in which the diamond particles are at least partially soluble. Milling beads are insoluble in organic solvents and therefore are not extracted into the organic solvent or solvents.

The organic solvent may be a non polar solvent or a polar solvent or a mixture of several solvents.

The reaction mixture from step b) may be first subjected to a centrifugation step or a mixing step or a filtration step to remove the majority of Milling beads. The resultant filtrate or supernatant may then be subjected to a further separation step, for example using a soxhlet extractor.

Preferably, the method of the invention further comprises the step of isolating the diamond particles in solid form. Separated diamond particles can be isolated by evaporation of excess organic or inorganic compound(s) or excess solvent(s). Alternatively, the diamond particles may be extracted into an organic solvent (or a mixture of solvents) and the diamond particles are isolated by evaporation of the organic solvent(s).

The method of the invention provides a simple method for the separation of diamond particle clusters into discrete diamond particles and/or smaller diamond particle clusters comprising fewer diamond particles by functionalizing the surface of the diamond particles with various chemical groups. The nature of these chemical groups is governed by the organic or inorganic compound(s) used in step a) of the process. There are very few steps to the method, resulting in increased yields, and the diamond particles produced are well dispersed in dry powder form, as well as in solution.

BRIEF DESCRIPTION OF THE DRAWINGS

In the drawings, which illustrate preferred embodiments of the invention:

FIG. 3a illustrates a bright-field (BF) image of separated nanodiamond particles;

FIG. 3b is a BF image of twinned particles;

FIGS. 3c and 3d illustrate a HAADF image of nanodiamond crystallinity;

FIG. 4a is a BF image of sparsely distributed nanodiamonds;

FIG. 4b is a magnification of a box-selected area in FIG. 4a;

FIG. 4c is a BF image of an isolated nanodiamond; and

FIG. 4d is an FFT analysis of the nanodiamond crystalline structure from FIG. 4c.

DETAILED DESCRIPTION OF THE PREFERRED EMBODIMENTS

Nanodiamonds used in the examples were produced by the detonation of explosives with a negative oxygen balance in hermetic tanks.

EXAMPLES

Example 1: Alkylation with 1-Undecene

The detonation nanodiamond powder was boiled in a mixture of concentrated sulphuric and perchloric acids (1:1)

for a period of two hours in order to remove any non-diamond forms of carbon. After this purification step the powder was dried in air at 50° C. to produce dry nanodiamond powder containing clusters of nanodiamonds.

200 mg of the dry nanodiamond powder was mixed with 1 g of zirconia/silica beads with an average diameter of approximately 0.1 mm. The mixture was placed in a plastic vial (2 ml) and filled with 1-undecene ($C_{11}H_{22}$).

The vial containing the mixture was shaken in a Mini-Beadbeater 3110BX (Stratech Scientific Ltd) at a frequency of 4500 Hz. Shaking was performed in cycles lasting 5 minutes. After each cycle the sample was cooled to avoid excessive heating by immersing the vial in water with a temperature of approximately 15° C. Shaking and cooling was repeated twelve times to give a total shaking time of 1 hour.

After shaking, the slurry containing the beads, the nanodiamonds and the 1-undecene was transferred to a Whatman cellulose extraction thimble and placed inside a Quickfit Sohxhlet exctrator to recover the nanodiamond material. Extraction of the nanodiamond particles was performed with undecane at 174° C. for 15 hours.

After the extraction, the solution was centrifuged at 16000 g for 1 hour.

The solution was left to evaporate completely to leave the alkylated nanodiamonds as a pale white powder residue.

Figure 1:
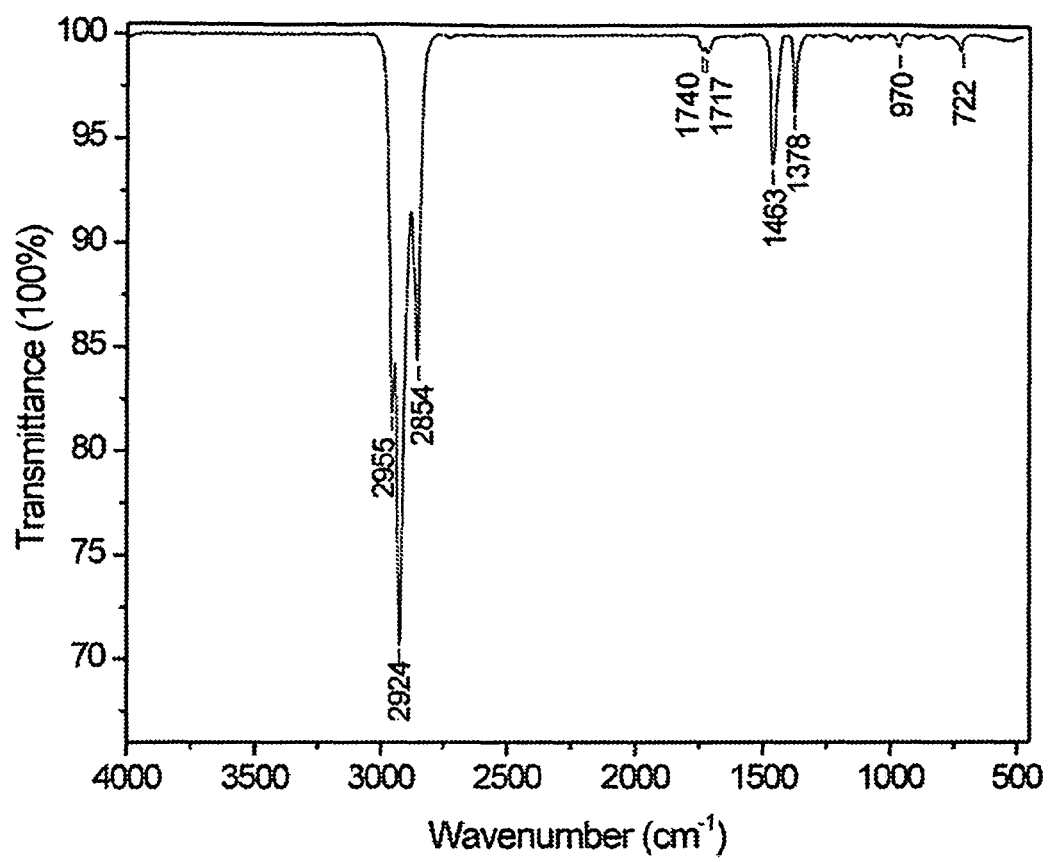
FIG. 1 is an FTIR spectrum of nanodiamonds alkylated with 1-undecene.

Confirmation of 1-undecene attachment to the nanodiamonds was performed by Fourier transform infrared spectroscopy (FTIR). FIG. 1 shows the FTIR spectrum of the alkylated nanodiamonds. The peak at 2955 cm$^{-1}$ indicates the presence of the —CH$_3$ asymmetric stretch mode, while bands at 2924 cm$^{-1}$ and 2854 cm$^{-1}$ confirm the presence of —CH$_2$ asymmetric and symmetric stretch modes. The appearance of a terminal methyl group can be demonstrated by vibrational absorption at 1463 and 1375 cm$^{-1}$ corresponding to C—CH$_3$ asymmetric and symmetric bending vibration, respectively. The complete absence of C=C groups which would appear at 1610-1680 cm$^{-1}$ confirms that the 1-undecene is involved directly in bonding to the surface. It is suggested that the π bond of the alkene is broken, transforming into a σ bond linking the alkene to the nanodiamond surface.

A sample of the alkylated nanodiamond powder was dissolved in pentane and several drops were deposited and allowed to dry upon a pre-cleaned, and Argon ion sputter tantalum foil for X-ray photoemission spectroscopy (XPS) characterisation.

Figure 2:
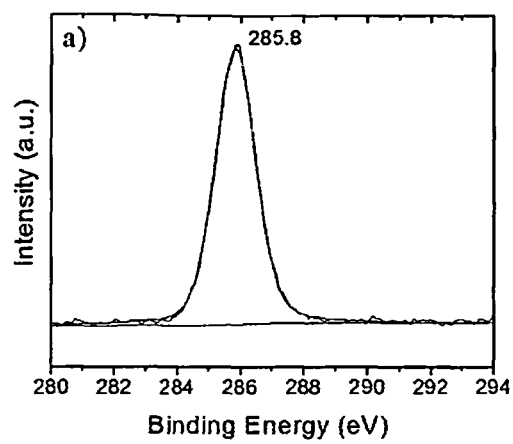
FIG. 2 is a C1s X-ray photoemission spectrum of nanodiamonds alkylated with 1-undence.

FIG. 2 illustrates the C1s X-ray photoemission spectrum of the nanodiamonds treated with 1-undecene. A single peak at a binding energy of 285.8 eV is observed, with a full width at half maximum (FWHM) of 1.7 eV indicating the presence of C—C sp$^3$ bonding within the material. This confirms that the sp$^2$ component present in pristine nanodiamond powder has been removed.

Figure 3:
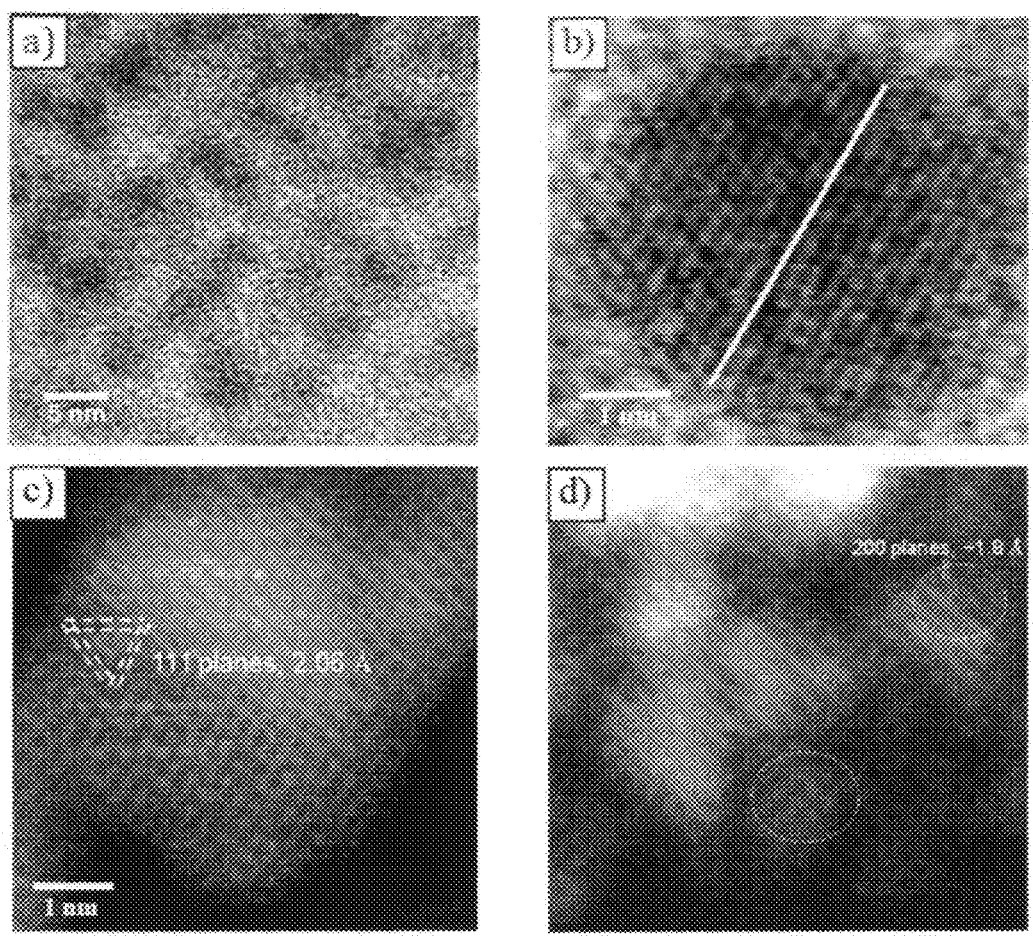
FIG. 3 illustrates Super STEM images of nanodiamond powder functionalised with 1-undecene that has been resuspended in solution and deposited by a drop cast method onto a carbon lacey TEM grid.

The SuperSTEM micrographs shown in FIG. 3 demonstrate that a solution of the alkyl-coated nanodiamonds with diameters of approximately 5 nm can be sparsely dispersed onto the surface of a lacey carbon TEM grid wand subsequently allowed to dry at ambient temperature (see FIG. 3a). FIGS. 3a and 3b confirm that the diamond particles are largely spherical in shape with an average diameter of 5 nm. These results confirm that the diamond particles remain as discrete particles after drying.

Figure 4:
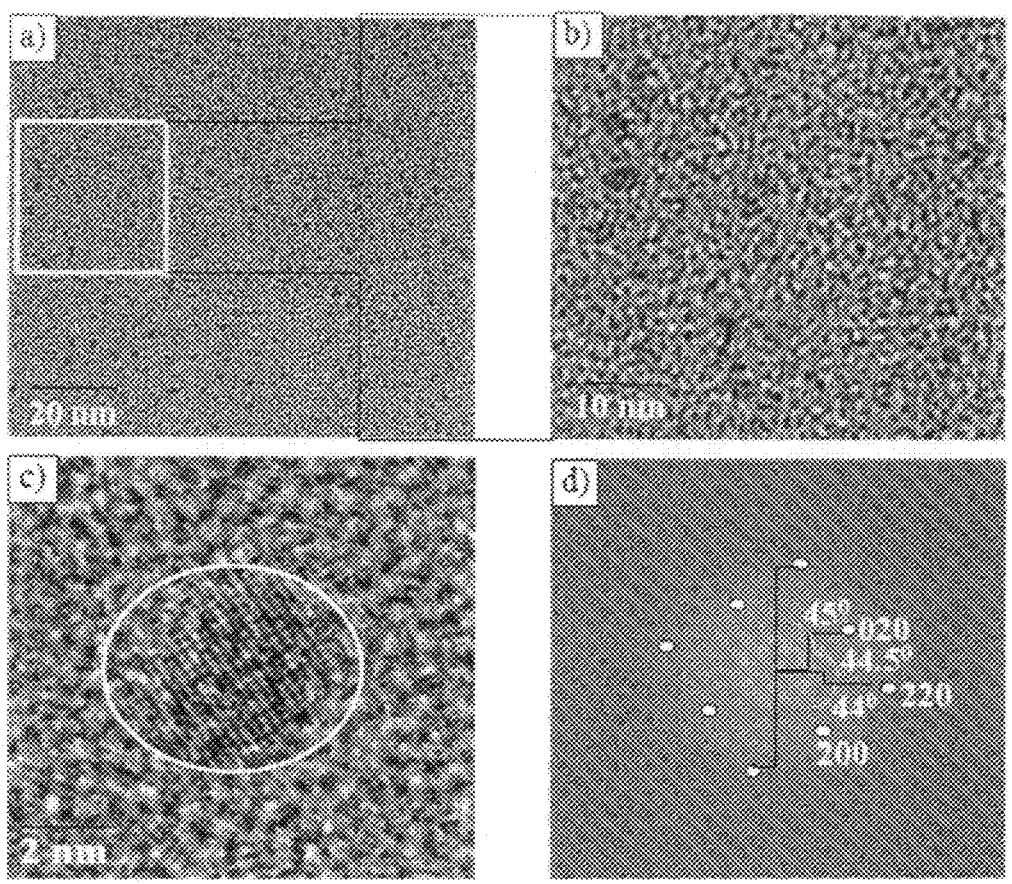
FIG. 4 illustrates HRTEM images and an associated fast Fourier transform (FFT) of evaporated nanodiamond powder evaporated at ~200° C. for 15 minutes, on a lacey carbon TEM grid.

FIG. 4 illustrates HRTEM images and an associated fast Fourier transform (FFT) of evaporated nanodiamond powder. FIG. 4a in particular illustrates that the diamond nanoparticles are well-separated and deposited successfully onto a lacey carbon grid by evaporation at ~200° C. for 15 minutes. Enlargement of the micrograph, FIG. 4b, shows that separated nanodiamond particles have diameters ranging from 2-4 nm. FIG. 3c shows an isolated particle with a diameter of 4 nm, which was subsequently used to determine the crystalline structure of the evaporated nanodiamonds. Determination of the crystal structure was carried out by FFT analysis which can be seen in FIG. 3d.

The invention claimed is:

1. A method for the separation of diamond particle clusters having a diameter of less than or equal to 1.0 mm into discrete diamond particles and/or into smaller clusters comprising fewer diamond particles, the method comprising the steps of:
    a) combining the diamond particle clusters with at least one liquid phase unsaturated organic compound, or with a solution of at least one unsaturated organic compound in at least one solvent, to form a reaction mixture, the unsaturated organic compound comprising at least one carbon-carbon double bond or carbon-carbon triple bond; and
    b) introducing milling beads to the reaction mixture and producing diamond particles with dangling bonds on the surface of the diamond particles by imparting kinetic energy to the diamond particle clusters within the reaction mixture using mechanical means to break up the diamond particle clusters into discrete diamond particles and/or into smaller clusters comprising fewer diamond particles causing the at least one unsaturated organic compound to react with at least some of the dangling bonds on the diamond particles;
    wherein imparting kinetic energy to the diamond particle clusters is performed in a plurality of cycles, with each cycle of imparting kinetic energy to the diamond particle clusters being followed by a period of cooling the reaction mixture.

2. A method according to claim 1, wherein step b) includes shaking or stirring the reaction mixture or applying ultrasonication to the reaction mixture.

3. A method according to claim 2, wherein the reaction mixture is shaken at a frequency of at least 10 Hz.

4. A method according to claim 2, wherein ultrasonication is applied to the reaction mixture at a frequency of not more than 80 kHz.

5. A method according to claim 1, wherein the milling beads are ceramic milling beads.

6. A method according to claim 5, wherein the milling beads are selected from the group comprising zirconia beads and silica beads and mixtures thereof.

7. A method according to claim 1, wherein the milling beads are larger than the diamond particles by a factor of between 100 and 100000.

8. A method according to claim 1, wherein the diamond particles have a diameter of 0.5 mm or less.

9. A method according to claim 1, wherein the diamond particles are nanodiamond particles and have a diameter in the range 1 to 1000 nm.

10. A method according to claim 1, wherein the at least one unsaturated organic compound is a straight chain alkene.

11. A method according to claim 1, wherein the at least one unsaturated organic compound is unsaturated at the first position.

12. A method according to claim 1, wherein the at least one unsaturated organic compound comprises a number of carbon atoms in the range 6 to 12.

13. A method according to claim 1, wherein the period of cooling the reaction mixture cools the liquid phase unsaturated organic compound to a temperature of not more than the boiling point of the reaction mixture.

14. A method according to claim 1, further comprising:
c) separating the discrete diamond particles from the milling beads.

15. A method according to claim 14, wherein in step c) the diamond particles are separated from the milling beads using a method selected from the group comprising: filtration, centrifugation, extraction, precipitation, decantation and combinations thereof.

16. A method according to claim 1, further comprising the step of isolating the discrete diamond particles in solid form.

17. A method for the separation of diamond particle clusters having a diameter of less than or equal to 1.0 mm into discrete diamond particles and/or into smaller clusters comprising fewer diamond particles, the method comprising the steps of:

a) combining the diamond particle clusters with at least one liquid phase unsaturated organic compound, or with a solution of at least one unsaturated organic compound in at least one solvent, to form a reaction mixture, the unsaturated organic compound comprising at least one carbon-carbon double bond or carbon-carbon triple bond; and b) creating diamond particles with dangling bonds on the surface of the diamond particles by imparting kinetic energy to the diamond particle clusters within the reaction mixture using mechanical means to break up the diamond particle clusters into discrete diamond particles and/or into smaller clusters comprising fewer diamond particles causing the at least one unsaturated organic compound to react with at least some of the dangling bonds on the diamond particles.

* * * * *